United States Patent [19]

Schneider

[11] Patent Number: 5,849,792
[45] Date of Patent: *Dec. 15, 1998

[54] STORAGE-STABLE PROSTAGLANDIN COMPOSITIONS

[75] Inventor: L. Wayne Schneider, Crowley, Tex.

[73] Assignee: Alcon Laboratories, Inc., Fort Worth, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 738,629

[22] Filed: Oct. 29, 1996

Related U.S. Application Data

[62] Division of Ser. No. 362,677, Dec. 22, 1994, Pat. No. 5,631,287.

[51] Int. Cl.⁶ ................................................ A61K 31/557
[52] U.S. Cl. ...................... 514/530; 514/570; 514/571; 514/573
[58] Field of Search .................... 514/573, 530, 514/570, 571

[56] References Cited

U.S. PATENT DOCUMENTS

| | | | |
|---|---|---|---|
| 4,075,333 | 2/1978 | Josse | 424/237 |
| 4,960,799 | 10/1990 | Nagy | 514/567 |
| 5,098,606 | 3/1992 | Nakajima | 252/358 |
| 5,110,493 | 5/1992 | Cherng-Chyi et al. | 514/413 |
| 5,185,372 | 2/1993 | Ushio et al. | 514/552 |

FOREIGN PATENT DOCUMENTS

| | | |
|---|---|---|
| 0 132 027 A1 | 1/1985 | European Pat. Off. . |
| 0 330 511 A2 | 6/1989 | European Pat. Off. . |
| 0 407 148 A3 | 1/1991 | European Pat. Off. . |
| 0 418 004 A2 | 3/1991 | European Pat. Off. . |
| 0 429 248 A2 | 5/1991 | European Pat. Off. . |
| 0 435 682 A2 | 7/1991 | European Pat. Off. . |
| 0 645 145 A3 | 3/1995 | European Pat. Off. . |
| 0 667 160 A2 | 8/1995 | European Pat. Off. . |
| WO 85/02841 | 12/1984 | WIPO . |
| WO 95/05163 | 2/1995 | WIPO . |

OTHER PUBLICATIONS

Attwood and Florence, "Reactivity in surfactant systems," *Surfactant Systems, Their Chemistry, Pharmacy and Biology*, 11:698–777, Chapman and Hall, Publ.

Foster et al., "Intraocular Penetration of Miconazole in Rabbits," Arch. ophthalmol. 97/9, pp. 1703–1706 (1979) (abstract only).

Sayed and Repta, "Solubilization and stabilization of an investigational antineoplastic drug (NSC No. 278214) in an intravenous formulation using an emulsion vehicle," *Internat'l J. of Pharmaceutics*, vol. 13 (1983), pp. 302–312.

*Primary Examiner*—Robert Gerstl
*Attorney, Agent, or Firm*—Patrick M. Ryan

[57] ABSTRACT

The use of polyethoxylated castor oils in prostaglandin compositions greatly enhances the prostaglandin's chemical stability.

13 Claims, 3 Drawing Sheets

Stability of 0.01% Compound No. 2. at 55°C in pH 5.0 Preserved Vehicle with the indicated Surfactant.

○ 0.5% Cremophor® EL
△ 0.5% Alkamuls® EL-620
◇ Polysorbate 80

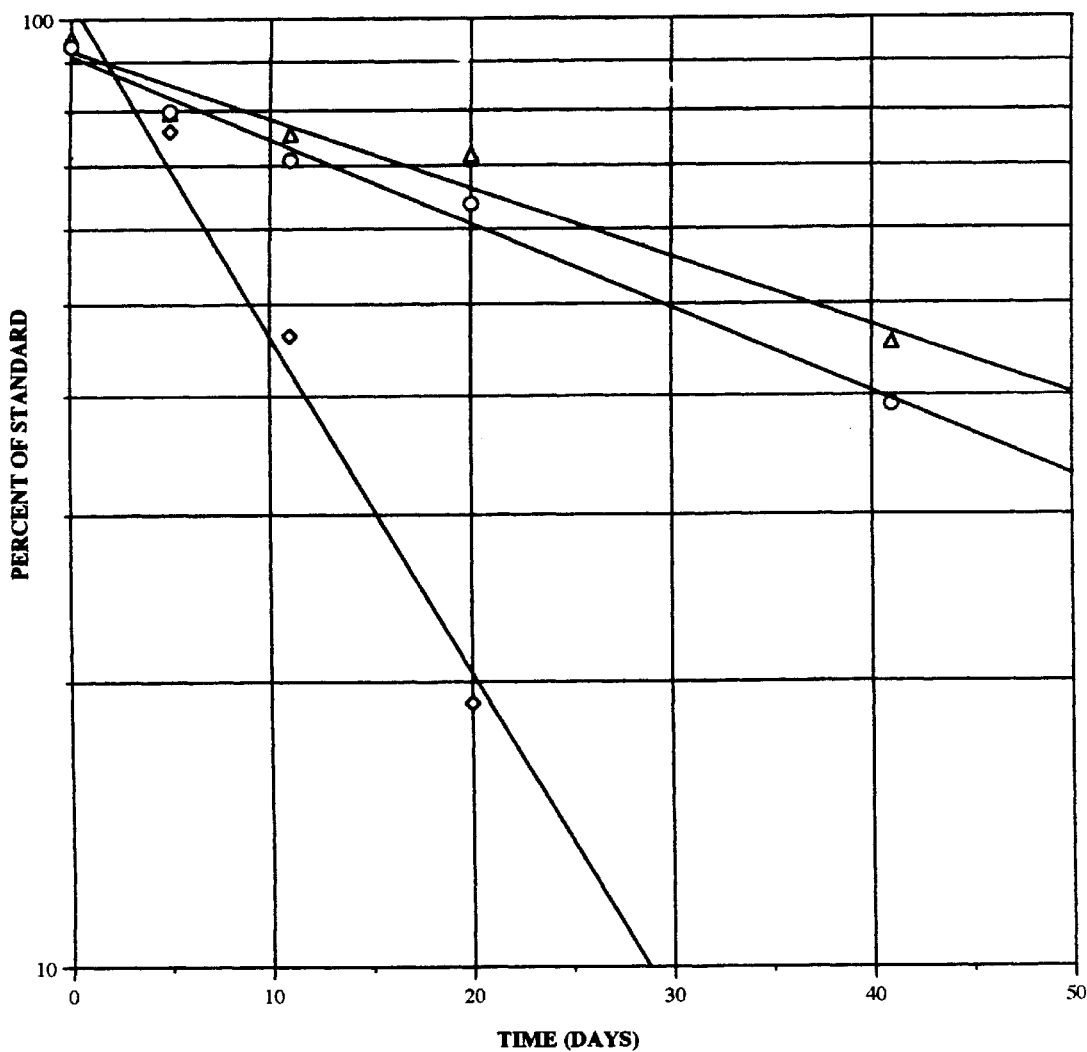

STORAGE-STABLE PROSTAGLANDIN COMPOSITIONS

This is a divisional application of U.S. patent application Ser. No. 08/362,677 filed on Dec. 22, 1994, now U.S. Pat. No. 5,631,287.

BACKGROUND OF THE INVENTION

The present invention relates generally to prostaglandin compositions. In particular, the present invention relates to storage stable, pharmaceutical compositions containing prostaglandins and surfactants. As used herein, the term "prostaglandin" or "PG" shall refer to prostaglandins and derivatives and analogues thereof including pharmaceutically acceptable salts and esters, except as otherwise indicated by context.

Prostaglandins have notoriously low water solubility, and are generally unstable. Attempts have been made to solubilize and stabilize various prostaglandins by complexing them with different cyclodextrins. See, for example: EP 330 511 A2 (Ueno et al.) and EP 435 682 A2 (Wheeler). These attempts have met with varying success.

Surfactants and/or solubilizers have been used with other types of drugs having low water solubility. However, the addition of surfactants and/or solubilizers may enhance or adversely affect the chemical stability of drug compounds. See *Surfactant Systems, Their Chemistry, Pharmacy, and Biology*, (eds. Attwood et al.), Chapman and Hall, New York, 1983, Ch. 11, particularly pp. 698–714.

The use of non-ionic surfactants, such as polyethoxylated castor oils, as solubilizing agents is known. See, for example, U.S. Pat. No. 4,960,799 (Nagy).

The use of non-ionic surfactants such as polyethoxylated castor oils in stable emulsions is also known. U.S. Pat. No. 4,075,333 (Josse) discloses stable, intravenous emulsion formulations of vitamins. El-Sayed et al., *Int. J. Pharm.*, 13:303–12 (1983) discloses stable oil-in-water emulsions of an antineoplastic drug. U.S. Pat. No. 5,185,372 (Ushio et al.) discloses topically administrable ophthalmic formulations of vitamin A which are stable preparations in which a non-ionic surfactant is used to form an emulsion of vitamin A in an aqueous medium.

What is needed is a commercially viable, storage-stable prostaglandin composition.

SUMMARY OF THE INVENTION

The present invention is directed to the use of polyethoxylated castor oils in pharmaceutical compositions containing prostaglandins. It has now been unexpectedly discovered that the use of such polyethoxylated castor oils in such compositions enhances the chemical stability of prostaglandins in pharmaceutical compositions. The compositions of the present invention can be administered to the body in a variety of ways. When topically applied to the eye, the compositions of the present invention provide both initial and continual comfort.

BRIEF DESCRIPTION OF THE DRAWINGS

FIG. 3 compares the stabilizing effect of different surfactants in a preserved prostaglandin formulation at pH 7.4.

DETAILED DESCRIPTION OF THE INVENTION

Figure 1:
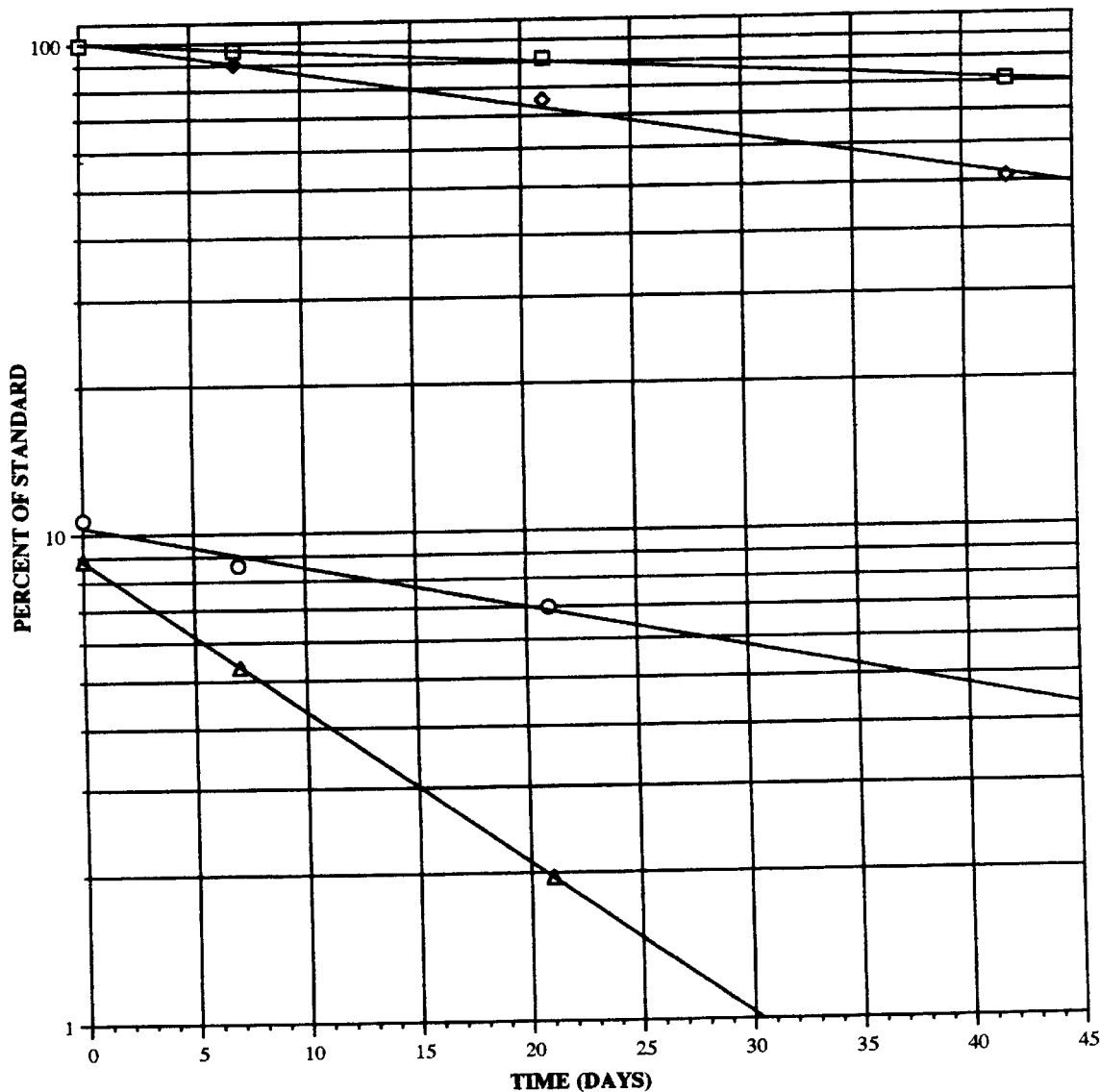
FIG. 1 shows the stabilizing effect at different concentrations of a polyethoxylated castor oil in a preserved prostaglandin formulation at pH 5.0.

Prostaglandin esters are difficult to formulate in storage-stable solutions as they tend to be hydrolytically unstable. In some instances, the parent acids of some prostaglandin esters are also unstable. The pharmaceutical compositions of the present invention, however, are storage stable. These compositions contain a prostaglandin and a stability-enhancing amount of a polyethoxylated castor oil.

The polyethoxylated castor oils useful in the compositions of the present invention are commercially available, and include those classified as PEG-2 to PEG-200 castor oils, as well as those classified as PEG-5 to PEG-200 hydrogenated castor oils. Such polyethoxylated castor oils include those manufactured by Rhone-Poulenc (Cranbury, N.J.) under the Alkamuls® brand, and those manufactured by BASF (Parsippany, N.J.) under the Cremophor® brand. It is preferred to use the polyethoxylated castor oils classified as PEG-15 to PEG-50 castor oils, and more preferred to use PEG-30 to PEG-35 castor oils. It is most preferred to use those polyethoxylated castor oils known as Cremophor® EL and Alkamuls® EL-620.

The terms "prostaglandin" and "PG" are generally used to describe a class of compounds which are analogues and derivatives of prostanoic acid (1):

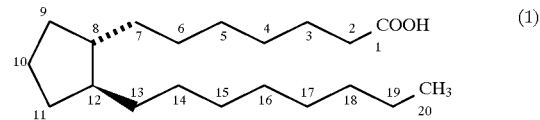

PG's may be further classified, for example, according to their 5-membered ring structure, using a letter designation:

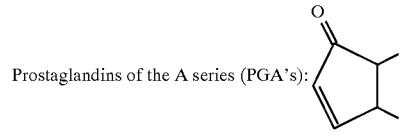

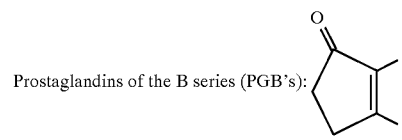

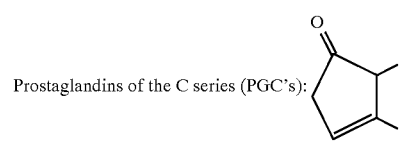

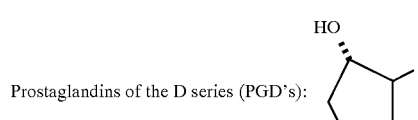

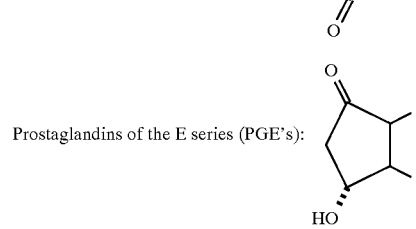

Prostaglandins of the F series (PGF's):

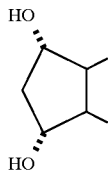

Prostaglandins of the J series (PGJ's):

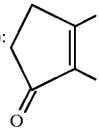

PG's may be further classified based on the number of unsaturated bonds on the side chain:

$PG_1$'s (13,14-unsaturated):

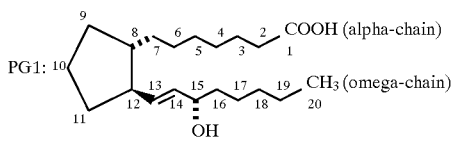

$PG_2$'s (13,14- and 5,6- unsaturated):

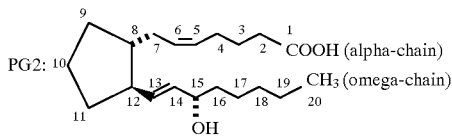

$PG_3$'s (13,14-5,6- and 17,18- unsaturated):

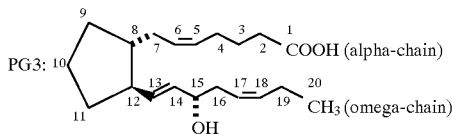

The prostaglandins which may be utilized in the present invention include all pharmaceutically acceptable prostaglandins, their derivatives and analogues, and their pharmaceutically acceptable esters and salts. Such prostaglandins include the natural compounds: $PGE_1$, $PGE_2$, $PGE_3$, $PGF_{1\alpha}$, $PGF_{2\alpha}$, $PGF_{3\alpha}$, $PGD_2$ and $PGI_2$ (prostacyclin), as well as analogues and derivatives of these compounds which have similar biological activities of either greater or lesser potencies. Analogues of the natural prostaglandins include but are not limited to: alkyl substitutions (e.g., 15-methyl or 16,16-dimethyl), which confer enhanced or sustained potency by reducing biological metabolism or alter selectivity of action; saturation (e.g., 13,14-dihydro) or unsaturation (e.g., 2,3-didehydro, 13,14-didehydro), which confer sustained potency by reducing biological metabolism or alter selectivity of action; deletions or replacements (e.g., 11-deoxy, 9-deoxo-9-methylene), chloro (or halogen) for oxygen (e.g., 9β-chloro), oxygen for carbon (e.g., 3-oxa), lower alkyl for oxygen (e.g., 9-methyl), hydrogen for oxygen (e.g., 1-$CH_2OH$,1-$CH_2OAcyl$) which enhance chemical stability and/or selectivity of action; and ω-chain modifications (e.g., 18,19,20-trinor-17-phenyl, 17,18,19,20-tetranor-16-phenoxy), which enhance selectivity of action and reduce biological metabolism. Derivatives of these prostaglandins include all pharmaceutically acceptable salts and esters, which may be attached to the 1-carboxyl group or any of the hydroxyl groups of the prostaglandin by use of the corresponding alcohol or organic acid reagent, as appropriate. It should be understood that the terms "analogues" and "derivatives" include compounds which exhibit functional and physical responses similar to those of prostaglandins per se.

Specific examples of prostaglandins which are useful in the present invention include the following compounds:

Compound No.
1. (5Z)-(9R,11R,15R)-9-chloro-15-cyclohexyl-11,15-dihydroxy-3-oxa-16,17,18,19,20-pentanor-5-prostenoic acid;
2. (5Z)-(9R,11R,15R)-9-chloro-15-cyclohexyl-11,15-dihydroxy-3-oxa-16,17,18,19,20-pentanor-5-prostenoic acid isopropyl ester;
3. (5Z)-(9R,11R,15R)-9-chloro-15-cyclohexyl-11,15-dihydroxy-3-oxa-16,17,18,19,20-pentanor-5-prostenoic acid t-butyl ester;
4. (5Z)-(9S,11R,15R)-15-cyclohexyl-3-oxa-9,11,15-trihydroxy-16,17,18,19,20-pentanor-5-prostenoic acid isopropyl ester;
5. (5Z)-(9R,11R,15S)-9-chloro-15-cyclohexyl-11,15-dihydroxy-3-oxa-16,17,18,19,20-pentanor-5-prostenoic acid isopropyl ester;
6. (5Z)-(9R,11R,15R)-9-chloro-15-cyclohexyl-11,15-dihydroxy-3-oxa-16,17,18,19,20-pentanor-5-prostenoic acid amide;
7. (5Z)-(9R,11R,15R)-9-chloro-15-cyclohexyl-11,15-dihydroxy-3-oxa-16,17,18,19,20-pentanor-5-prostenoic acid N,N-dimethylamide;
8. (5Z)-(9R,11R,15R)-9-chloro-15-cyclohexyl-11,15-dihydroxy-3-oxa-16,17,18,19,20-pentanor-5-prostenoic acid 1-methylcyclohexyl ester;
9. (5Z)-(9R,11R,15R)-9-chloro-15-cyclohexyl-11,15-dihydroxy-3-oxa-16,17,18,19,20-pentanor-5-prostenoic acid 1-methylcyclopentyl ester;
10. (5Z)-(9R,11R,15R)-9-chloro-15-cyclohexyl-11,15-dihydroxy-3-oxa-16,17,18,19,20-pentanor-5-prostenoic acid cyclopentyl ester;
11. (5Z)-(9R,11R,15R)-9-chloro-15-cyclohexyl-11,15-dihydroxy-3-oxa-16,17,18,19,20-pentanor-5-prostenoic acid 2,2-dimethylpropyl ester;
12. (5Z)-(9R,11R,15R)-9-chloro-15-cyclohexyl-11,15-dihydroxy-3-oxa-16,17,18,19,20-pentanor-5-prostenoic acid adamantyl ester;
13. (5Z)-(9R,11R,15R)-9-chloro-15-cyclohexyl-11,15-dihydroxy-3-oxa-16,17,18,19,20-pentanor-5-prostenoic acid 2,6-diisopropylphenyl ester;
14. (5Z)-(9R,11R,15R)-9-chloro-15-cyclohexyl-11,15-dihydroxy-3-oxa-16,17,18,19,20-pentanor-5-prostenoic acid 2,6-dimethylphenyl ester;
15. (5Z, 13E)-(9S,11R,15R)-3-oxa-9,11,15-trihydroxy-16-(3-chlorophenoxy)-17,18,19,20-tetranor-5,13-prostadienoic acid isopropyl ester;
16. (5Z)-(9R,11R,15R)-9-chloro-15-cyclohexyl-11-hydroxy-15-methoxy-3-oxa-16,17,18,19,20-pentanor-5-prostenoic acid t-butyl ester;
17. (5Z)-(9R,11R,15R)-15-cyclohexyl-3-oxa-9,11,15-trihydroxy-16,17,18,19,20-pentanor-5-prostenoic acid isopropyl ester;
18. (5E)-(9R,11R,15R)-9-chloro-15-cyclohexyl-11,15-dihydroxy-3-oxa-16,17,18,19,20-pentanor-5-prostenoic acid isopropyl ester;
19. (5Z)-(9R,11R)-9-chloro-15-cyclohexyl-11-hydroxy-3-oxa-15-oxo-16,17,18,19,20-pentanor-5-prostenoic acid tertbutyl ester;

20. (5Z)-(9S,11R,15R)-3-oxa-17-phenyl-9,11,15-trihydroxy-18,19,20-trinor-5-prostenoic acid isopropyl ester;
21. (5Z)-(9R,11R,15R)-9-chloro-15-cyclohexyl-1-(dimethylamino)-3-oxa-16,17,18,19,20-pentanor-5-prostene-11,15-diol;
22. (5Z)-(9R,11R,15R)-9-chloro-15-cyclohexyl-11,15-dihydroxy-3-oxa-16,17,18,19,20-pentanor-5-prostenol;
23. (9R,11R,15R)-9-chloro-15-cyclohexyl-11-hydroxy-3-thia-16,17,18,19,20-pentanor-13-prostynoic acid;
24. Latanoprost (PhXA41);
25. Cloprostenol isopropyl ester;
26. (5Z)-(9S,11R,15R)-1-decarboxy-1-(pivaloyloxy)methyl-9,11,15-trihydroxy-16-[(3-chlorophenyl)oxy]-17,18,19,20-tetranor-5-prostenoic acid;
27. (5Z)-(9S,11R,15R)-1-decarboxy-1-(pivaloyloxy)methyl-9,11,15-trihydroxy-16-[(3-chlorophenyl)oxy]-17,18,19,20-tetranor-5,13-prostadienoic acid;
28. (5Z)-(9R,11R,15R)-9-chloro-15-cyclohexyl-11,15-dihydroxy-16,17,18,19,20-pentanor-5-prostenoic acid isopropyl ester;
29. (5Z)-(9S,11R,15S)-15-cyclohexyl-9,11,15-trihydroxy-16,17,18,19,20-pentanor-5-prostenoic acid isopropyl ester;
30. (5Z, 13E)-(9S,11R,15R)-9,11,15-trihydroxy-16-(3-clorophenoxy)-17,18,19,20-tetranor-5,13-prostadienoic acid amide;
31. $PGF_{2\alpha}$ isopropyl ester; and
32. Fluprostenol isopropyl ester.

All of the foregoing compounds are known. Preferred prostaglandins for use in the compositions of the present invention are Compounds 2–8 above. Most preferred are Compounds 2 and 3 above. The structures of Compounds 2 and 3 are shown below.

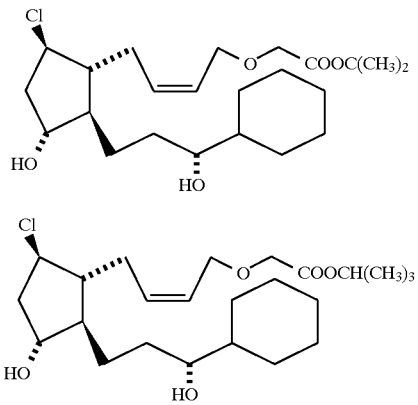

The prostaglandin compositions of the present invention contain one or more polyethoxylated castor oils in an amount effective to enhance the stability of the prostaglandin. As FIG. 1 illustrates the stabilizing effect of the polyethoxylated castor oil increases with increasing polyethoxylated castor oil concentration. However, other factors may limit the amount of polyethoxylated castor oil to be utilized in the compositions of the present invention. For example, too much polyethoxylated castor oil should not be used in order to avoid adversely affecting the prostaglandin's pharmacologic activity.

In general, compositions of the present invention will include one or more polyethoxylated castor oils in an amount between about 0.02 and about 20.0 percent by weight (wt %) and one or more prostaglandins in an amount between about 0.00001 and about 0.2 wt %. It is preferred to use one or more polyethoxylated castor oils in an amount between about 0.1 and about 5.0 wt %, is and it is especially preferred to use an amount between about 0.5 and about 2.0 wt %. It is preferred to use one or more prostaglandins in an amount between about 0.0001 and about 0.1 wt %, depending on the potency of the prostaglandin.

The compositions of the present invention may be administered to the body in a variety of ways. The compositions may be administered by mouth, by intravenous injection or by topical application to the skin, nose or eyes. Most preferred are compositions prepared for topical administration to the eye.

In addition to the above-described principal active ingredients, the compositions of the present invention may further comprise various formulatory ingredients, such as antimicrobial preservatives, tonicity agents, and buffers. Examples of suitable antimicrobial preservatives include: benzalkonium chloride, thimerosal, chlorobutanol, methyl paraben, propyl paraben, phenylethyl alcohol, edetate disodium, sorbic acid, Polyquad® and other agents equally well known to those skilled in the art. Such preservatives, if utilized, will typically be employed in an amount between about 0.001 and about 1.0 wt %. Examples of suitable agents which may be utilized to adjust the tonicity or osmolality of the formulations include sodium chloride, potassium chloride, mannitol, dextrose, glycerine and propylene glycol. Such agents, if utilized, will be employed in an amount between about 0.1 and about 10.0 wt %. Examples of suitable buffering agents include acetic acid, citric acid, carbonic acid, phosphoric acid, boric acid, the pharmaceutically acceptable salts of the foregoing, and tromethamine. Such buffers, if utilized, will be employed in an amount between about 0.001 and about 1.0 wt %.

The compositions of the present invention may additionally include components to provide sustained release and/or comfort. Such components include high molecular weight, anionic mucomimetic polymers and gelling polysaccharides, such as those described in U.S. Pat. No. 4,861,760 (Mazuel et al), U.S. Pat. No. 4,911,920 (Jani et al.), and in commonly assigned U.S. Ser. No. 08/108,824 (Lang et al.). The contents of these patents and patent applications relating to the polymers cited above are incorporated herein by reference.

As will be appreciated by those skilled in the art, the compositions may be formulated in various dosage forms suitable for topical ophthalmic delivery, including solutions, suspensions, emulsions, gels and erodible solid ocular inserts. The compositions are preferably aqueous, have a pH between 3.5 to 8.0 and an osmolality between 260 to 320 milliOsmoles per kilogram (mOsm/kg).

The present invention is also directed to methods of treating glaucoma and other ophthalmic diseases and abnormalities. The methods comprise topically applying to the affected eye(s) of the patient a therapeutically effective amount of a composition according to the present invention. The frequency and amount of dosage will be determined by the clinician based on various clinical factors. The methods will typically comprise topical application of one or two drops (approximately 30 microliters) of a liquid composition, or an equivalent amount of a solid or semi-solid dosage form, to the affected eye one to two times per day.

EXAMPLE

The following topically administrable ophthalmic formulations are representative of the compositions of the present invention.

| FORMULATION (wt %) | | | |
|---|---|---|---|
| INGREDIENT | A | B | C |
| Compound 2 | 0.01 | — | 0.01 |
| Compound 3 | — | 0.01 | — |
| Cremophor ® EL | 0.5 | 0.5 | 0.5 |
| Sodium Acetate (Trihydrate) | 0.07 | 0.07 | — |
| Tromethamine | — | — | 0.12 |
| Boric Acid | — | — | 0.3 |
| Mannitol | 4.6 | 4.6 | 4.6 |
| Disodium EDTA | 0.1 | 0.1 | 0.1 |
| Benzalkonium Chloride | 0.01 | 0.01 | 0.01 |
| NaOH and/or HCl | q.s. to pH 5 | q.s. to pH 5 | q.s. to pH 7 |
| Purified Water | q.s. to 100% | q.s. to 100% | q.s. to 100% |

Preparation of Formulations A–C

To a clean glass vessel of appropriate size was added approximately 75% of the batch volume of water. To this was sequentially added sodium acetate, tromethamine, boric acid, mannitol, EDTA, benzalkonium chloride and Cremophor® EL so that there was complete dissolution of one ingredient prior to the addition of the next ingredient. Next the pH of the solution was adjusted using NaOH and/or HCl, and the water was added to bring the volume to 100%.

In a separate clean glass vessel, the appropriate quantity of prostaglandin was added, followed by the appropriate quantity of the vehicle whose preparation was described above. The vessel was then tightly capped and sonicated in an ultrasonic bath for one hour or alternatively stirred with a magnetic stir bar overnight, until the prostaglandin was completely dissolved. The resulting solution was then sterile filtered (0.2 micron filter) into sterile containers. These containers were then aseptically plugged, capped and labelled.

The stabilizing effect of polyethoxylated castor oils in the compositions of the present invention was evaluated according to the following procedure.

1. Pipet the required quantity of 1% w/v prostaglandin ethanolic stock solution into 1.5 mL high performance liquid chromatograph (HPLC) sample vials.
2. Dry the sample vials under a stream of helium.
3. Add 1 mL of the appropriate vehicle (or HPLC mobile phase for standards).
4. Sonicate the vials one hour to dissolve the prostaglandin.
5. Run initial HPLC assays.
6. Place the HPLC sample vials into 20 cc scintillation vials with several mLs of deionized water and cap tightly. (Note: This prevents loss due to evaporation.) Standards are stored with HPLC mobile phase in the scintillation vial.
7. Place the vials in the appropriate controlled temperature ovens and reassay periodically by HPLC. Standards are stored in a refrigerator.
8. HPLC Data Analysis: Divide Sample Peak Area by Standard Peak Area and multiply by 100 to obtain Percent of Standard for each sample at each time point.
9. Plot Percent of Standard versus time on a semilogarithmic graph. Fit a monoexponential equation to the data. The slope times 2.303 is the apparent first-order degradation rate constant for each plot (Note: The factor of 2.303 converts common logarithm to natural logarithm).

FIG. 1 demonstrates the effect of increasing polyethoxylated castor oil concentration in Formulation A. The chemical stability of a given concentration of prostaglandin is increased as the concentration of Cremophor® EL is increased.

Figure 2:
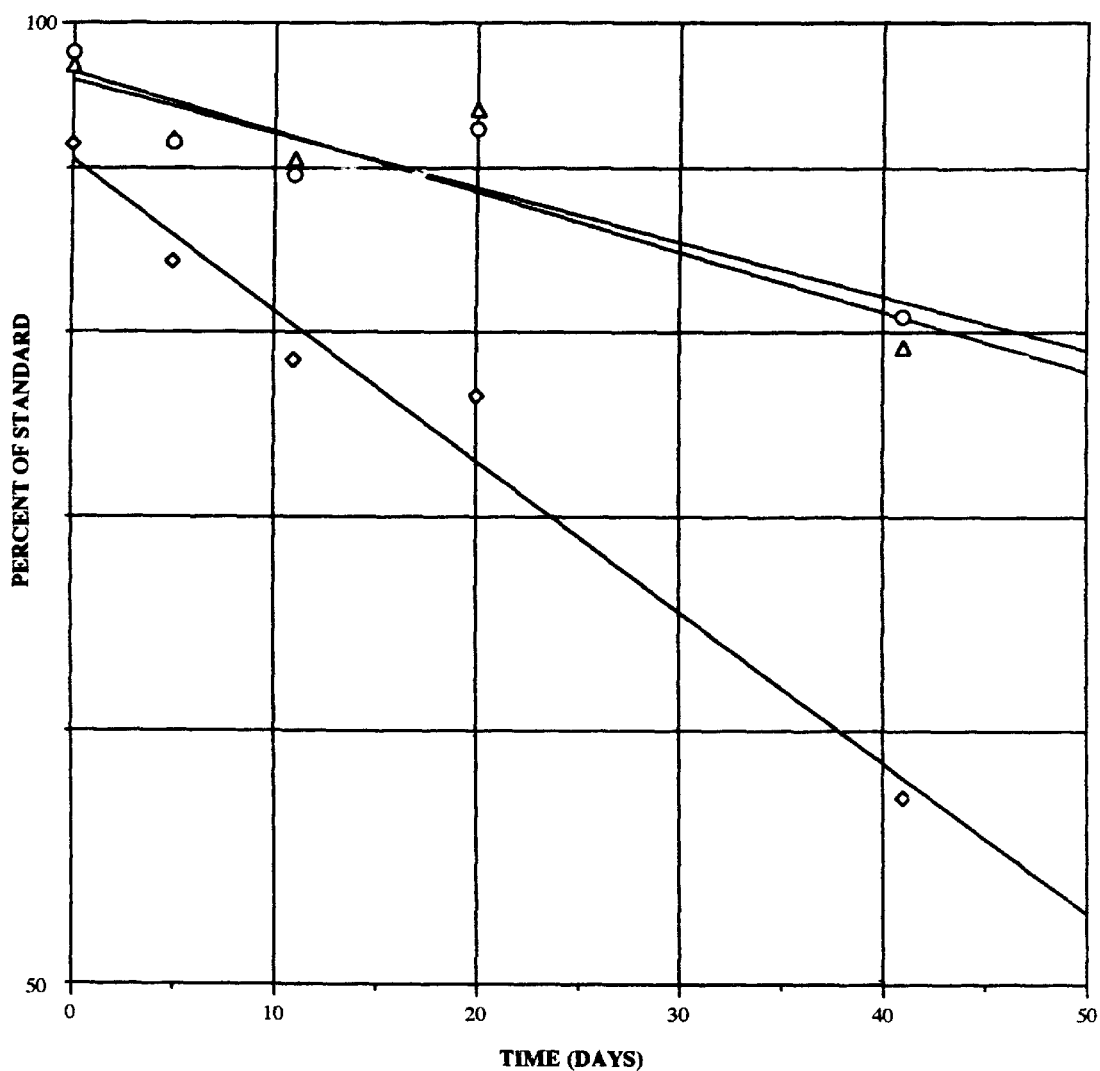
FIG. 2 compares the stabilizing effect of different surfactants in a preserved prostaglandin formulation at pH 5.0.

FIG. 2 demonstrates the superior stabilizing effect of the polyethoxylated castor oils, Cremophor® EL and Alkamuls® EL-620, over Polysorbate 80 in a type A Formulation (pH=5.0).

FIG. 3 demonstrates the superior stabilizing effect of the polyethoxylated castor oils, Cremophor® EL and Alkamuls® EL-620, over Polysorbate 80 in a type C formulation (pH=7.4).

The data shown in FIGS. 1–3 were generated using a Phenomenex 250×4.6 mm HPLC column with Spherisorb® 10 ODS(2) packing. The mobile phase was 50/50 acetonitrile/0.1% phosphoric acid at pH 3 with NaOH, 5 mM tetrabutylammonium hydroxide, and 5 mM sodium dodecylsulfate. The flow rate was 2 mL/minute, the detection was 190–192 nm UV, and the injection quantity was 25 mcL.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. An aqueous pharmaceutical composition comprising a prostaglandin, a polyethoxylated castor oil in an amount effective to enhance the chemical stability of the prostaglandin, an antimicrobial preservative and a pharmaceutically acceptable vehicle.

2. The composition of claim 1 wherein the polyethoxylated castor oil is present at a concentration between about 0.02 wt % and about 20.0 wt %.

3. The composition of claim 2 wherein the polyethoxylated castor oil is present at a concentration between about 0.1 wt % and about 5.0 wt %.

4. The composition of claim 3 wherein the polyethoxylated castor oil is present at a concentration between about 0.5 wt % and about 2.0 wt %.

5. The composition of claim 1 wherein the polyethoxylated castor oil is selected from the group consisting of: PEG-2 to PEG-200 castor oils and PEG-5 to PEG-200 hydrogenated castor oils.

6. The composition of claim 5 wherein the polyethoxylated castor oil is selected from the group consisting of: PEG-15 to PEG-50 castor oils.

7. The composition of claim 6 wherein the polyethoxylated castor oil is selected from the group consisting of: PEG-30 to PEG-35 castor oils.

8. The composition of claim 1 wherein the prostaglandin is selected from the group consisting of (5Z)-(9R,11R,15R)-9-chloro-15-cyclohexyl-11,15-dihydroxy-3-oxa-16,17,18,19,20-pentanor-5-prostenoic acid; (5Z)-(9R,11R,15R)-9-chloro-15-cyclohexyl-11,15-dihydroxy-3-oxa-16,17,18,19,20-pentanor-5-prostenoic acid isopropyl ester; (5Z)-(9R,11R,15R)-9-chloro-15-cyclohexyl-11,15-dihydroxy-3-oxa-16,17,18,19,20-pentanor-5-prostenoic acid t-butyl ester; (5Z)-(9S,11R,15R)-15-cyclohexyl-3-oxa-9,11,15-trihydroxy-16,17,18,19,20-pentanor-5-prostenoic acid isopropyl ester; (5Z)-(9R,11R,15S)-9-chloro-15-cyclohexyl-11,15-dihydroxy-3-oxa-16,17,18,19,20-pentanor-5-prostenoic acid isopropyl ester; (5Z)-(9R,11R,15R)-9-chloro-15-cyclohexyl-11,15-dihydroxy-3-oxa-16,17,18,19,20-pentanor-5-prostenoic acid amide; (5Z)-(9R,11R,15R)-9-chloro-15-cyclohexyl-11,15-dihydroxy-3-oxa-16,17,18,19,20-pentanor-5-prostenoic acid N,N-dimethylamide; (5Z)-(9R,11R,15R)-9-chloro-15-cyclohexyl-11,15-dihydroxy-3- oxa-16,17,18,19,20-pentanor-5-prostenoic acid 1-methylcyclohexyl ester; (5Z)-(9R,11R,15R)-9-chloro-15-cyclohexyl-11,15-dihydroxy-3-oxa-16,17,18,19,20-pentanor-5-prostenoic acid 1-methylcyclopentyl ester; (5Z)-(9R,11R,15R)-9-chloro-15-cyclohexyl-11,15-dihydroxy-3-oxa-16,17,18,19,20-pentanor-5-prostenoic acid cyclopentyl ester; (5Z)-(9R,11R,15R)-9-chloro-15-cyclohexyl-11,15-dihydroxy-3-oxa-16,17,18,19,20-pentanor-5-prostenoic acid 2,2-dimethylpropyl ester; (5Z)-(9R,11R,15R)-9-chloro-15-cyclohexyl-11,15-dihydroxy-3-oxa-16,17,18,19,20-pentanor-5-prostenoic acid adamantyl ester; (5Z)-(9R,11R,15R)-9-chloro-15-cyclohexyl-11,15-dihydroxy-3-oxa-16,17,18,19,20-pentanor-5-prostenoic acid 2,6-diisopropylphenyl ester; (5Z)-(9R,11R,15R)-9-chloro-15-cyclohexyl-11,15-dihydroxy-3-oxa-16,17,18,19,20-pentanor-5-prostenoic acid 2,6-dimethylphenyl ester; (5Z,13E)-(9S,11R,15R)-3-oxa-9,11,15-trihydroxy-16-(3-chlorophenoxy)-17,18,19,20-tetranor-5,13-prostadienoic acid isopropyl ester; (5Z)-(9R,11R,15R)-9-chloro-15-cyclohexyl-11-hydroxy-15-methoxy-3-oxa-16,17,18,19,20-pentanor-5-prostenoic acid t-butyl ester; (5Z)-(9R,11R,15R)-15-cyclohexyl-3-oxa-9,11,15-trihydroxy-16,17,18,19,20-pentanor-5-prostenoic acid isopropyl ester; (5E)-(9R,11R,15R)-9-chloro-15-cyclohexyl-11,15-dihydroxy-3-oxa-16,17,18,19,20-pentanor-5-prostenoic acid isopropyl ester; (5Z)-(9R,11R)-9-chloro-15-cyclohexyl-11-hydroxy-3-oxa-15-oxo-16,17,18,19,20-pentanor-5-prostenoic acid tertbutyl ester; (5Z)-(9S,11R,15R)-3-oxa-17-phenyl-9,11,15-trihydroxy-18,19,20-trinor-5-prostenoic acid isopropyl ester; (5Z)-(9R,11R,15R)-9-chloro-15-cyclohexyl-1-(dimethylamino)-3-oxa-16,17,18,19,20-pentanor-5-prostene-11,15-diol; (5Z)-(9R,11R,15R)-9-chloro-15-cyclohexyl-11,15-dihydroxy-3-oxa-16,17,18,19,20-pentanor-5-prostenol; 9R,11R,15R)-9-chloro-15-cyclohexyl-11-hydroxy-3-thia-16,17,18,19,20-pentanor-13-prostynoic acid; latanoprost (PhXA41); cloprostenol isopropyl ester; (5Z)-(9S,11R,15R)-1-decarboxy-1-(pivaloyloxy)methyl-9,11,15-trihydroxy-16-[(3-chlorophenyl)oxy]-17,18,19,20-tetranor-5-prostenoic acid; (5Z)-(9S,11R,15R)-1-decarboxy-1-(pivaloyloxy)methyl-9,11,15-trihydroxy-16-[(3-chlorophenyl)oxy]-17,18,19,20-tetranor-5,13-prostadienoic acid; (5Z)-(9R,11R,15R)-9-chloro-15-cyclohexyl-11,15-dihydroxy-16,17,18,19,20-pentanor-5-prostenoic acid isopropyl ester; (5Z)-(9S,11R,15S)-15-cyclohexyl-9,11,15-trihydroxy-16,17,18,19,20-pentanor-5-prostenoic acid isopropyl ester; (5Z, 13E)-(9S,11R,15R)-9,11,15-trihydroxy-16-(3-chlorophenoxy)-17,18,19,20-tetranor-5,13-prostadienoic acid amide; $PGF_{2\alpha}$ isopropyl ester; and fluprostenol isopropyl ester.

9. The composition of claim 8 wherein the prostaglandin is selected from the group consisting of: (5Z)-(9R,11R,15R)-9-chloro-15-cyclohexyl-11,15-dihydroxy-3-oxa-16,17,18,19,20-pentanor-5-prostenoic acid isopropyl ester; (5Z)-(9R,11R,15R)-9-chloro-15-cyclohexyl-11,15-dihydroxy-3-oxa-16,17,18,19,20-pentanor-5-prostenoic acid t-butyl ester; (5Z)-(9S,11R,15R)-15-cyclohexyl-3-oxa-9,11,15-trihydroxy-16,17,18,19,20-pentanor-5-prostenoic acid isopropyl ester; (5Z)-(9R,11R,15S)-9-chloro-15-cyclohexyl-11,15-dihydroxy-3-oxa-16,17,18,19,20-pentanor-5-prostenoic acid isopropyl ester; (5Z)-(9R,11R,15R)-9-chloro-15-cyclohexyl-11,15-dihydroxy-3-oxa-16,17,18,19,20-pentanor-5-prostenoic acid amide; (5Z)-(9R,11R,15R)-9-chloro-15-cyclohexyl-11,15-dihydroxy-3-oxa-16,17,18,19,20-pentanor-5-prostenoic acid N,N-dimethylamide; and (5Z)-(9R,11R,15R)-9-chloro-15-cyclohexyl-11,15-dihydroxy-3-oxa-16,17,18,19,20-pentanor-5-prostenoic acid 1-methylcyclohexyl ester.

10. The composition of claim 9 wherein the prostaglandin is selected from the group consisting of (5Z)-(9R,11R,15R)-9-chloro-15-cyclohexyl-11,15-dihydroxy-3-oxa-16,17,18,19,20-pentanor-5-prostenoic acid isopropyl ester and (5Z)-(9R,11R,15R -9-chloro-15-cyclohexyl-11,15-dihydroxy-3-oxa-16,17,18,19,20-pentanor-5-prostenoic acid t-butyl ester.

11. The composition of claim 1 wherein the prostaglandin is present at a concentration between about 0.0001 wt % and about 0.1 wt %.

12. The composition of claim 1 wherein the composition is a topically administrable ophthalmic composition.

13. An method for the treatment of glaucoma and ocular hypertension, comprising the topical administration to an affected eye of an aqueous composition comprising a prostaglandin, a polyethoxylated castor oil, an antimicrobial preservative and an ophthalmically acceptable vehicle, wherein the polyethoxylated castor oil is present in an amount effective to enhance the chemically stability of the prostaglandin.

* * * * *